United States Patent [19]

Chen et al.

[11] Patent Number: 5,585,470
[45] Date of Patent: Dec. 17, 1996

[54] PROCESS FOR THE MANUFACTURE OF 3-AMINO-SUBSTITUTED GLYCOSYLATED BILE ACIDS

[75] Inventors: Anna K. Chen, Rahway; Ramesh Kakarla; Dashan Liu, both of East Brunswick; Michael J. Sofia, Lawrenceville; Thomas C. Zebovitz, Colonia, all of N.J.

[73] Assignee: Transcell Technologies, Inc., Monmouth Junction, N.J.

[21] Appl. No.: 264,310

[22] Filed: Jun. 23, 1994

[51] Int. Cl.$^6$ .............................. C07G 3/00; C07G 17/00; C07H 15/24
[52] U.S. Cl. ................. 536/5; 536/18.5; 536/124
[58] Field of Search ................. 536/5, 18.5, 124

[56] References Cited

U.S. PATENT DOCUMENTS 5,338,837  8/1994  DiKahne ........................... 536/5

FOREIGN PATENT DOCUMENTS 9311772  6/1994  WIPO .............................. A61K 31/56

OTHER PUBLICATIONS

Kahne, D., et al., *J. Am. Chem. Soc.* (1989) 111:6881–6882.
Blickenstaff, R., et al., *J. of Chem.*, (1973) 38(7):1276–1279.
Blickenstaff, R., et al., *J. of Chem.*, (1971) 36(9):1271–1276.
Werner and Wess, *Tet. Lett.*, (1992) 33(2):195–198.
Fiegel, Martin, *Tet. Lett.*, (1994) 35(4):565–568 (and German language version, *Chem. Abstract*, 115:P72019d).

*Primary Examiner*—John W. Rollins
*Attorney, Agent, or Firm*—Lowe, Price, LeBlanc & Becker

[57] ABSTRACT

The present invention relates to a process for the preparation and manufacture of 3-amino-substituted glycosylated bile acid derivatives. Novel intermediates and related compounds are also disclosed.

27 Claims, 9 Drawing Sheets

PROCESS FOR THE MANUFACTURE OF 3-AMINO-SUBSTITUTED GLYCOSYLATED BILE ACIDS

BACKGROUND OF THE INVENTION

1. Field of the Invention

The present invention relates to a process for the synthesis and manufacture of 3-amino-substituted glycosylated bile acid derivatives. In particular, the present invention permits the conversion of cholic acid esters to the 3-amino-7,12-bis(glycosyl)cholic acid esters via an azide intermediate. Conditions for the purification and isolation of the desired product is also disclosed to provide an overall manufacturing process suitable for large-scale production.

2. Background of the Invention

The 3-amino-substituted glycosylated bile acid derivatives are disclosed in International Publication No. WO 93/11772. These and their related compounds are described as permeation enhancers; that is, these compounds enhance the ability of therapeutically significant compounds to penetrate biological or synthetic membranes. This property of permeation enhancement is observed whether the therapeutically significant compound is combined with the permeation enhancer as an admixture or as a conjugate therewith.

Hence, from a commercial point of view, an efficient synthetic scheme for the preparation of such permeation enhancers, particularly the 3-amino-substituted glycosylated bile acid derivatives, would be extremely attractive.

SUMMARY OF THE INVENTION

Accordingly, it is an object of the present invention to provide a process for the synthesis and manufacture of 3-amino-substituted glycosylated bile acids. Generally, the synthesis can be achieved from a widely available starting material, such as cholic acid. After esterification of the cholic acid side chain, the 3-hydroxy group is converted to a suitable leaving group, such as a tosylate, preferably a mesylate. Nucleophilic displacement of the leaving group, with inversion of stereochemistry, is performed using an azide reagent. Subsequently, the resulting 3-azido derivative is subjected to a sulfoxide-based bisglycosylation procedure to provide the 3-azido-substituted bisglycosylated cholic acid ester. Reduction of the azido group to the corresponding amine, followed by removal of any protecting groups present on the sugar moieties, provides the desired 3-amino-substituted glycosylated bile acid.

Other objects of the present invention include the disclosure of isolation and purification methods, including a description of the solvent mixtures suitable for recrystallization of reagents, intermediates, or products, as well as purification of selected compounds by reverse-phase column chromatography.

DETAILED DESCRIPTION OF THE PREFERRED EMBODIMENTS

Figure 1:
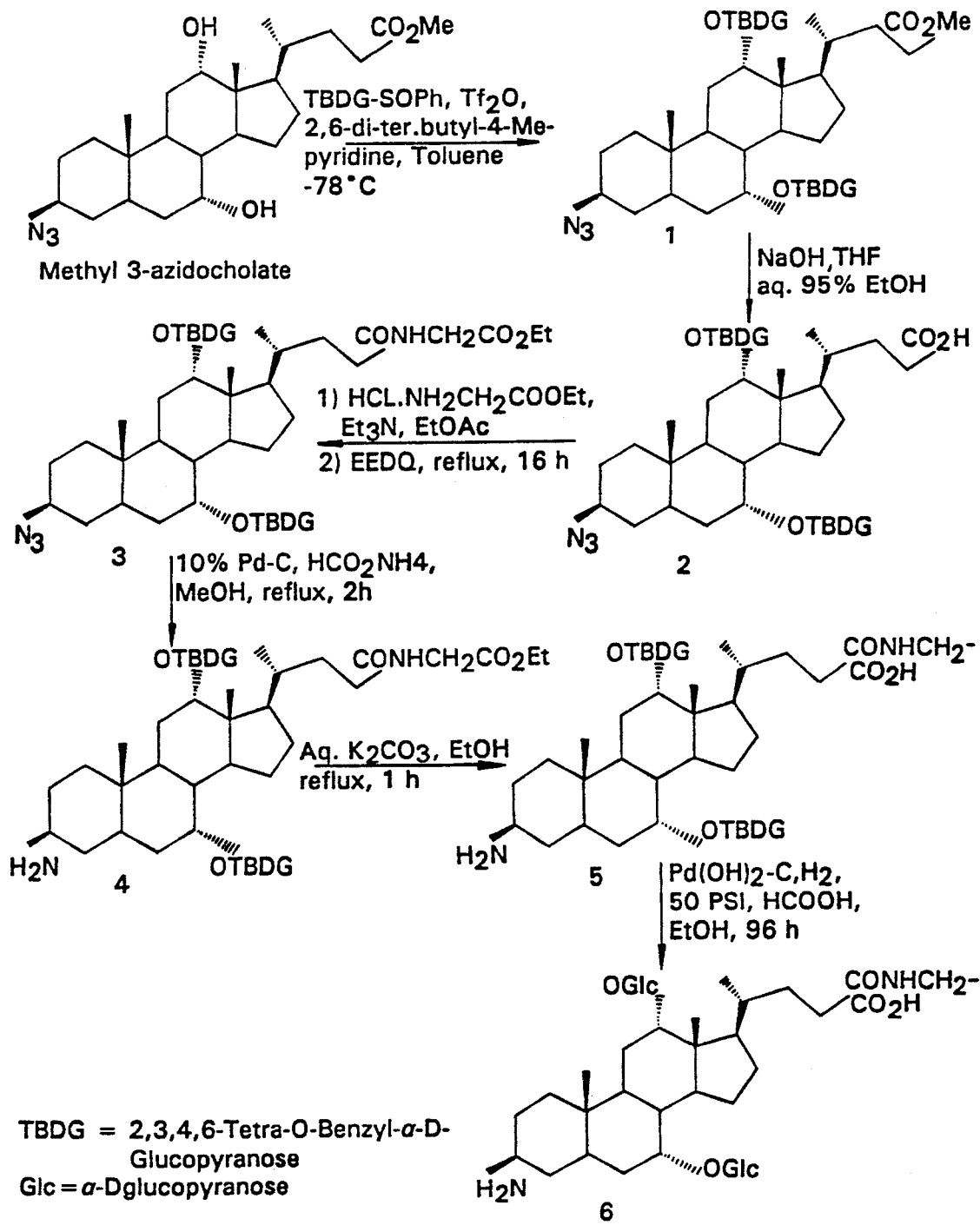
FIG. 1. Synthetic scheme for the preparation of 3β-amino-7α, 12α-di(1'α-glucosyl)-5β-cholan-24-oic acid N-[carboxymethyl]amide.

In the process of the present invention, a cholic acid ester compound is converted to an intermediate bearing a leaving group at the 3-position of the steroid nucleus. In a specific embodiment, the leaving group is chosen from among a tosylate or a mesylate, preferably the latter. Thus, methyl cholic acid ester is treated in dry pyridine with a slight excess of methanesulfonyl chloride to provide the 3-mesylate intermediate. The hydroxy groups C-7 and C-12 do not react with the reagent under appropriate conditions (e.g., at 0° C.). Other solvents for the reaction include, but are not limited to, methylene chloride and methylene chloride/pyridine mixtures, optionally, in the presence of a small amount of dimethylaminopyridine.

Subsequently, the leaving group is displaced by an azido group with inversion of the stereochemistry at C-3 to provide the 3-azido-substituted cholic acid ester. Thus, the 3-mesylate or tosylate is treated with sodium azide, preferably in excess. Suitable solvents include, but are not limited to, dimethylformamide, N-methylpyrrolidone, and the like. The reaction is typically carried out at elevated temperature.

This 3-azido intermediate is then glycosylated at the open hydroxyl groups using the glycosyl sulfoxide chemistry first described by Kahne, D. et al. in *J. Am. Chem. Soc.* (1989) 111:6881–6882. Additional guidance on the glycosylation step can be found in International Publication No. WO 93/11772. The complete disclosure of these publications are incorporated by their reference herein. Typically, the 3-azido cholic acid ester is dissolved in toluene, mixed with the desire glycosyl sulfoxide, and treated with an activating agent, such as triflic anhydride, at low temperature to initiate the condensation reaction.

Reduction of the 3-azido-substituted glycosylated cholic acid ester derivative is then accomplished in a number of ways, usually with the protecting groups of the sugar moieties in place. For instance, reduction to give the amine is effected by treating the 3-azido-substituted glycosylated intermediate with ammonium formate and palladium on carbon, triphenyl phosphine or Raney nickel. Reduction can also be effected by treatment with lithium aluminum hydride, although this method is accomplished by reduction of any ester groups present in the starting material. Useful solvents include aqueous tetrahydrofuran and the like. Preferably, the reaction is carried out at elevated temperature. Thus, for example, a sealable reaction vessel is charged with 0.5 g of the 3-azido compound 8, illustrated in FIG. 4, and dissolved in 6 mL of an ethyl acetate/methanol solvent mixture (2:1, v/v). Wet activated Raney nickel (ca. 1 g) is then added to the vessel, which is then sealed and pressurized with hydrogen to 50 psi. The reaction vessel and its content are heated to 55° C. for 1 h. After cooling, the vessel is depressurized and its contents filtered. The resulting filtrate is concentrated to provide ca. 0.5 g of a colorless oil, identified as the corresponding 3-amino-substituted bisglycosyl cholic acid methyl ester 9, illustrated in FIG. 4.

Subsequently, hydrolysis of the glycosyl protecting groups, typically benzyl, pivaloyl or isopropylidine groups provides the 3-amino-substituted glycosylated bile acid ester derivative which can be purified using reverse phase column chromatography. Hydrolysis can be effected by treatment of the protected glycoside with palladium hydroxide on carbon in a protic medium (e.g., an ethanol/toluene solvent mixture in the presence of formic or acetic acid), followed by hydrogenolysis.

In a preferred embodiment of the present invention, the 3-amino product is purified by elution through an MCI CHP-20P reverse-phase gel column (available from Mitsubishi Chemical) using an aqueous methanol eluent (e.g., a gradient of 0–50% methanol in water or an isocratic solution of 25% methanol in water). The final product is isolated from the chromatography solvent under reduced pressure and preferably freeze-dried to provide the pure solid.

Accordingly, the methods disclosed herein provide a number of 3-amino-substituted glycosylated bile acid derivatives and intermediates to their synthesis, including cholic acid, allocholic acid, deoxycholic acid or chenodeoxycholic acid derivatives, depending on the starting material. Specific intermediates of note, include the 3β-azido-7α,12α-di(1'α-glucosyl)-5β-cholic acid, its salt, ester or amide or the compound 3α-azido-7α,12α-di(1'α-glucosyl)-5β-cholic acid, its salt, ester or amide.

Furthermore, a novel difluoro cholane derivative is also disclosed, 3β,24-difluoro-7α,12α-di(1'α-glucosyl)-5β-cholane. It is believed that this compound will exhibit permeation enhancing characteristics and, thus, will be useful in facilitating the penetration of diagnostic, prophylactic or therapeutic agents across biological or synthetic membranes, particularly, mucosal membranes.

Figure 9:
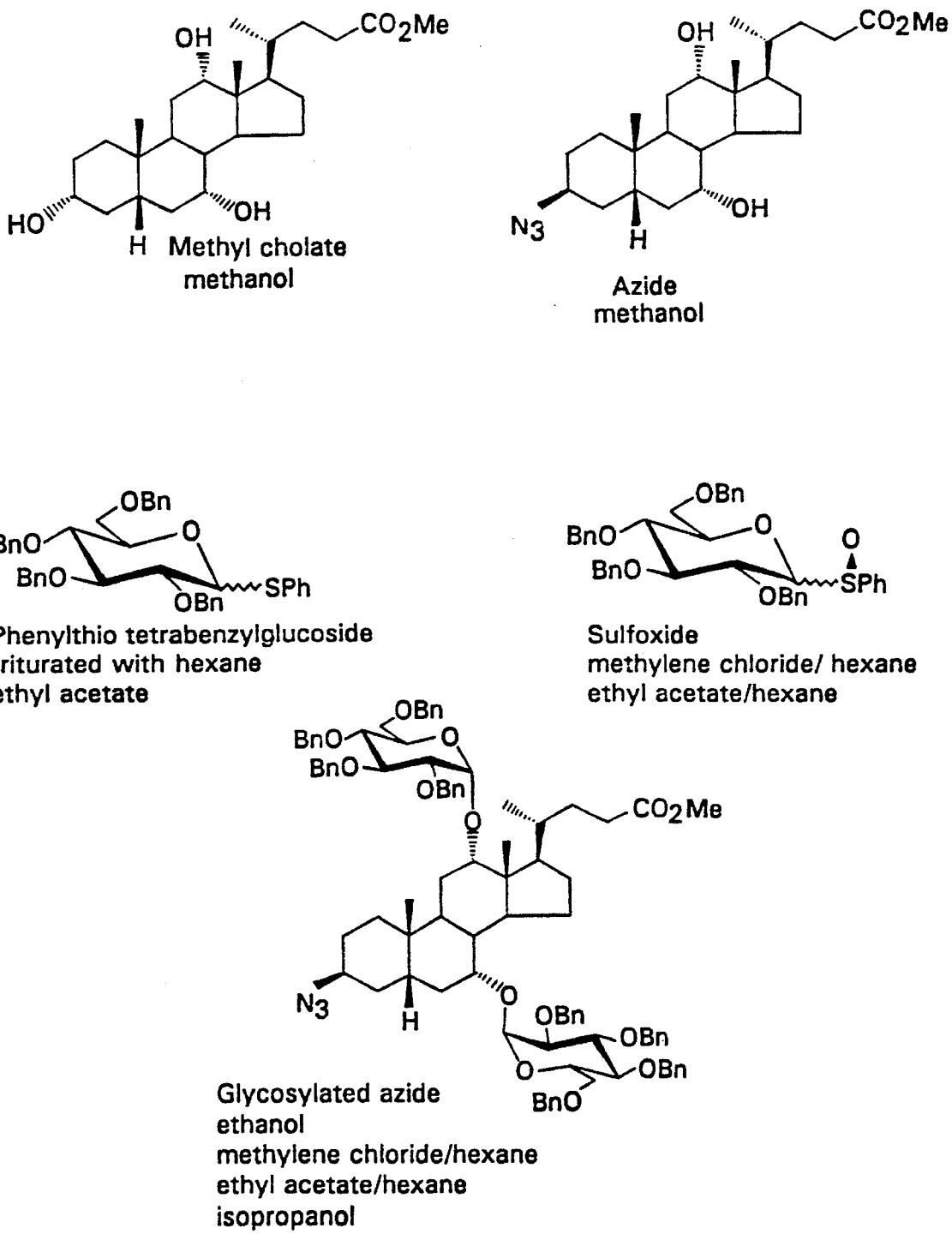
FIG. 9. Listing of solvent or solvent mixtures for recrystallization of selected reagents, intermediates or products.

In addition, FIG. 9 lists selected solvents or solvent mixtures from which various reagents, intermediates or products described herein may be recrystallized to provide purer compounds.

As a further illustration of the present invention, the following examples are provided, which describe in further detail the general aspects of the present process.

EXAMPLES

Example 1

Synthesis of 3β-Amino-7α, 12α-di(1'α-glucosyl)-5β-cholan-24-oic acid N-[carboxymethyl]amide (6) (See, FIG. 1).

Reactions are generally run under a positive pressure of dry nitrogen. Anhydrous solvents are used unless water is involved in the reaction. Flash chromatography employs Merck silica gel (Kieselgel 60, 200–400 mesh). TLC is performed with 0.2 mm coated commercial silica gel plates (E. Merck, Kieselgel 60 $F_{254}$). Melting points are determined using a Mel-Temp 11 (Laboratory Devices) capillary-melting-point apparatus in open capillary tubes and are uncorrected. Microanalysis are performed by Atlantic Microlab, Inc., Norcross, Ga. Infrared Spectra are recorded on Midac Prospect-IR (FT-IR) and reported in wavenumbers ($cm^{-1}$). Proton NMR spectra are measured at 300 MHz on a Varian instrument. Chemical shifts are reported in ppm downfield from TMS. 1.1. Methyl 3β-azido-5β-cholate.

A mixture of methyl 3-O-mesylcholate (40 g, 80 mmol) and sodium azide (26 g, 400 mmol) in 2-methylpyrrolidone (200 mL) is heated at 105° C. for 3 h. Afterward the reaction mixture is poured into ice-cold water and stirred for 15 min. After filtration, the solids are washed with water (1 L) and air dried. Recrystallization of the precipitate from methanol (125 mL) gives 32.18 g (90%) of methyl 3-azidocholate as white needles (mp 148°–149° C.). TLC (solvent-EtOAC: Hexane=3:2) $R_f$=0.5. IR (KBr): 3448, 2938, 2868, 2097, 1730 $cm^{-1}$. $^1$H NMR (CDCl$_3$): δ4.05 (s, 1H), 3.95 (d, 1H), 3.67 (s, 3H), 2.62–0.70 (M, 36H). Fab MS: 470 (M+Na)$^+$.

1.2. Methyl 3β-azido-7α,12α-di-(2', 3', 4', 6'-tetra-O-benzyl-1'α-glucosyl)-5β-cholate (1).

Triflic anhydride (9.24 mL, 55 mmol) is added to cooled (−78° C.) toluene (100 mL) solvent with stirring for 5 min. To this solution, dried (by azeotropic distillation from toluene) phenyl 2,3,4,6-tetra-O-benzyl-D-glucopyranosyl-1-sulfoxide (32.43 g, 50 mmol), dissolved in toluene (100 mL), is added dropwise. After 15 min of stirring, a solution of dried (by azeotropic distillation from toluene) 2,6-di-terbutyl-4-methyl-pyridine (8.21 g, 40 mmol) in toluene (20 mL) is added to the reaction mixture and stirred for 10 min at −78° C. To this reaction mixture, dried (by azeotropic distillation from toluene) methyl 3-azidocholate (8.94 g, 20 mmol) in CH$_2$Cl$_2$ and toluene (1:4, 50 Ml) is added dropwise. The reaction progress is monitored by TLC. The temperature of the reaction mixture is slowly allowed to rise to −60° C. over 45 min. During this time, the TLC spot due to methyl 3-azidocholate completely disappears. The reaction mixture is then poured into saturated aqueous sodium bicarbonate (250 mL) and stirred for 10 min. The organic layer is separated, and the aqueous layer is extracted with dichloromethane (2×50 mL). The organic layers are combined and washed with water (3×250 mL), dried (Na$_2$SO$_4$), and concentrated. The residue is purified by flash chromatography (EtOAC:Hexane=1:9 to 1:4) to furnish 1 (12 g, 40%), which is immediately recrystallized (EtoAC:Hexane= 1:5) to give 9 g (30%) of product as needles (mp 112°–114° C.). TLC (solvent-EtOAC:Hexane=1:4) $R_f$=0.6.

IR (KBr): 3085, 3061, 3029, 2921, 2867, 2097, 1735, 1603, 1495, 1452, 1360, 1256, 1207, 1160, 1091, 1071, 1031 $cm^{-1}$. $^1$H NMR (CDCl$_3$): δ7.37–6.84 (m, 40H), 5.15 (d, 1H, J=4 Hz), 4.95 (d, 1H, J=4 Hz), 4.86–4.26 (m, 15H), 4.08–3.40 (m, 16H), 2.60–0.71 (m, 36H). Fab MS: 1515 (M+Na)$^+$. Anal. Calc. for C$_{93}$H$_{110}$O$_{14}$N$_3$: C, 74.76; H, 7.43; N, 2.81. Found: C, 74.84; H, 7.40; N, 2.79.

1.3. 3β-Azido-7α,12α-Di-(2', 3', 4', 6'-tetra-O-benzyl-1'α-glucosyl)-5β-cholan-24oic acid (2).

To a stirred solution of 1 (4.1 g, 2.75 mmol) in THF (50 mL), is added NaOH (1.1 g, 27.5 mmol) in 95% aqueous ethanol (50 mL). The mixture is heated under reflux for 1.5 h. The mixture is then allowed to cool and is concentrated to provide a residue, which is dissolved in ethyl acetate (100 mL), washed consecutively with water (2×50 mL), saturated aqueous sodium bicarbonate (2×50 mL), and brine (100 mL). After drying (Na$_2$SO$_4$), the solvent is evaporated to afford pure 2 (3.86 g, 95%) as a white foam (mp 60°–62° C.). TLC (solvent-EtOAC:Hexane=3:7) $R_f$=0.2. IR (KBr): 3420, 3080, 3057, 3030, 2922, 2868, 2097, 1735, 1725, 1707, 1496, 1451, 1362, 1273, 1147, 1070 $cm^{-1}$. $^1$H NMR (CDCl$_3$): δ7.20–6.85 (m, 40H), 5.03 (d, 1H, J=3 Hz), 5.02 (d, 1H, J=3Hz), 4.85–3.20 (m, 28H), 2.62–0.77 (m, 36H). Fab MS: 1502 (M+Na)$^+$. Anal. Calc. for C$_{92}$H$_{108}$O$_{14}$N$_3$: C, 74.66; H, 7.36; N, 2.84. Found: C, 74.68; H, 7.18; N, 2.79.

1.4. 3β-Azido-7α,12α-di-(2', 3', 4', 6'-tetra-O-benzyl-1'α-glucosyl)-5β-cholan-24-oic acid N-[ethyl methylcarboxylate]amide (3).

To a suspension of ethylglycine hydrochloride (420 mg, 3 mmol) in ethyl acetate (100 mL) is added triethylamine (3 mL) with stirring at 40° C. for 1 h. The compound 2 (2.986 g, 2 mmol) and ethyl 1,2-dihydro-2-ethoxy-1-quinolinecarboxylate (EEDQ) (988 mg, 4 mmol) in ethylacetate (100 mL) are then added to this mixture, which is then heated under reflux for 16 h. Afterward, the mixture is cooled, washed successively with 0.5N aqueous NaOH (100 mL), 0.5N aqueous HCl (100 mL), and water (2×200 mL). After drying ($Na_2SO_4$), the solvent is evaporated. The residue is purified by flash chromatography ($EtOH:CH_2Cl_2$=1:19) to give 3 (2.66 g, 85%) as a white foam (mp 46°–47° C.). TLC (solvent-$EtOH:CH_2Cl_2$=1:19) $R_f$=0.3. IR (KBr): 3410, 3351, 3088, 3060, 3032, 2924, 2098, 1746, 1674, 1503, 1454, 1366, 1262, 1050 $cm^{-1}$. $^1$H NMR ($CDCl_3$): δ7.25–6.85 (m, 40H), 5,82 (brs, 1H), 5.15 (m, 2H), 4.84–3.40 (m, 30H), 2.60–0.65 (m, 39H). Fab MS: 1586 $(M+Na)^+$. Anal. Calc. for $C_{96}H_{115}O_{15}N_4$: C, 73.67; H, 7.41; N, 3.88. Found: C, 73.45; H, 7.46; N, 3.60.

1.5. 3β-Amino-7α,12α-di(2', 3', 4', 6'-tetra-O-benzyl-1'α-glucosyl)-5β-cholan-24oic acid N-[ethyl methylcarboxylate]amide (4)

To a solution of compound 3 (2.35 g, 1.5 mmol) in ethylacetate (40 mL) and methanol (60 mL) is added ammonium formate (1.26 g, 20 mmol) and 10% palladium on carbon (anhydrous, 200 mg). The contents of the reaction vessel are heated under reflux for 6 h. After filtration through Celite® (15 g), the filtrate is concentrated, dissolved in methylene chloride (100 mL), and washed with water (200 mL). After drying ($Na_2SO_4$), the solution is concentrated. The residue is separated into its components by flash chromatography: starting material 3 (500 mg, using 5% ethanol in methylene chloride) and, with 10% ethanol in methylene chloride, product 4 (1.155 g, 50%) as a white foam (mp 64°–66° C.). TLC (solvent-$EtOH:CH_2Cl_2$=1:9) $R_f$=0.3. IR (KBr): 3426, 3358, 3090, 3065, 3045, 3012, 2925, 2869, 1741, 1670, 1613, 1520, 1454, 1363, 1321, 1211, 1157, 1085 $cm^{-1}$. $^1$H NMR ($CDCl_3$): δ7.27–6.90 (m, 40H), 5.81 (brs, 1H), 4.99 (brs, 2H), 4.85–3.40 (m, 25H), 3.24–3.18 (m, 1H), 3.10–3.02 (br s, 1H), 2.92–2.88 (m, 1H), 2.60–0.60 (m, 39H). Fab MS: 1559 $(M+Na)^+$. Anal. Calc. for $C_{96}H_{117}O_{15}N_2$: C, 74.91; H, 7.67; N, 1.82. Found: C, 74.74; H, 7.64; N, 1.86.

1.6. 3β-Amino-7α,12α-di-(2', 3', 4', 6'-tetra-O-benzyl-1'α-glucosyl)-5β-cholan-24oic acid N-[carboxymethyl]amide (5).

To a refluxing solution of compound 4 (770 mg, 0.5 mmol) in ethanol (25 mL), 10% aqueous potassium carbonate (1 mL) is added. Heating under reflux is continued for an additional 1 h. The mixture is concentrated and diluted with methylene chloride (50 mL). The organic layer is washed with water (2×50 mL) and dried ($Na_2SO_4$). Evaporation of the solvent furnished 5 (683 mg, 90%) as a white powder (mp 150°–152° C.). TLC (solvent-$EtOH:CH_2Cl_2$=1:9) $R_f$=0.1. IR (KBr): 3414, 3086, 3061, 3030, 2923, 2868, 1659, 1640, 1628, 1601, 1497, 1452, 1387, 1159, 1088, 1070, 1028 $cm^{-1}$. $^1$H NMR ($CDCl_3$): δ7.35–6.85 (m, 40H), 6.20 (br s, 1H), 5.10–3.48 (m, 32H), 3.00–0.60 (m, 36H). Fab MS: 1531 $(M+Na)^+$. Anal. Calc. for $C_{94}H_{113}O_{15}N_2$: C, 74.71; H, 7.54; N, 1.85. Found: C, 74.58; H, 7.76; N, 1.90.

1.7. 3β-Amino-7α,12α-di-(-1'α-glucosyl)-5β-cholan-24-oic acid N-[carboxymethyl]amide (6).

To a solution of 5 (605 mg, 0.4 mmol) in ethanol (100 mL), formic acid (1.5 mL) and palladium hydroxide (20%) on carbon (600 mg) are added. The resulting mixture is hydrogenated at 50 psi for 24 h. TLC indicates incomplete hydrogenolysis. Additional formic acid (1.5 mL) is added and hydrogenation is allowed for another 24 h. Additional formic acid and further hydrogenation can be added and performed as warranted. The reaction mixture is then filtered through sand and a membrane filter and concentrated. The residue is precipitated with EtOAc and filtered. The precipitate is dissolved in 25 mL deionized water and freeze-dried. Reverse-phase column chromatography of the residue over CHP-20 (water followed by MeOH:Water=1:1) gives 189 mg (60%) of 6 as a white foam (mp>275° C., decomp.). TLC (solvent-$MeOH:CH_2Cl_2$:Isopropylamine=2:2:1) $R_f$=0.15. IR (KBr): 3394, 2932, 2878, 2870, 1640, 1630, 1619, 1598, 1389, 1150, 1023 $cm^{-1}$. $^1$HNMR ($D_2O$): δ5.35–5.33 (m, 1H), 5.08 (d, 1H, J=3 Hz), 4.87 (d, 1H, J=3 Hz), 3.98 (br s, 1H), 3.80–3.24 (m, 14H), 2.60–0.65 (m, 37H). Fab MS: 781 $(M+Na)^+$. Anal. Calc. for $C_{38}H_{64}O_{15}N_2.3H_2O$: C, 54.13; H, 8.37; N, 3.32. Found: C, 54.35; H, 8.43; N, 3.25.

Example 2

Figure 2:
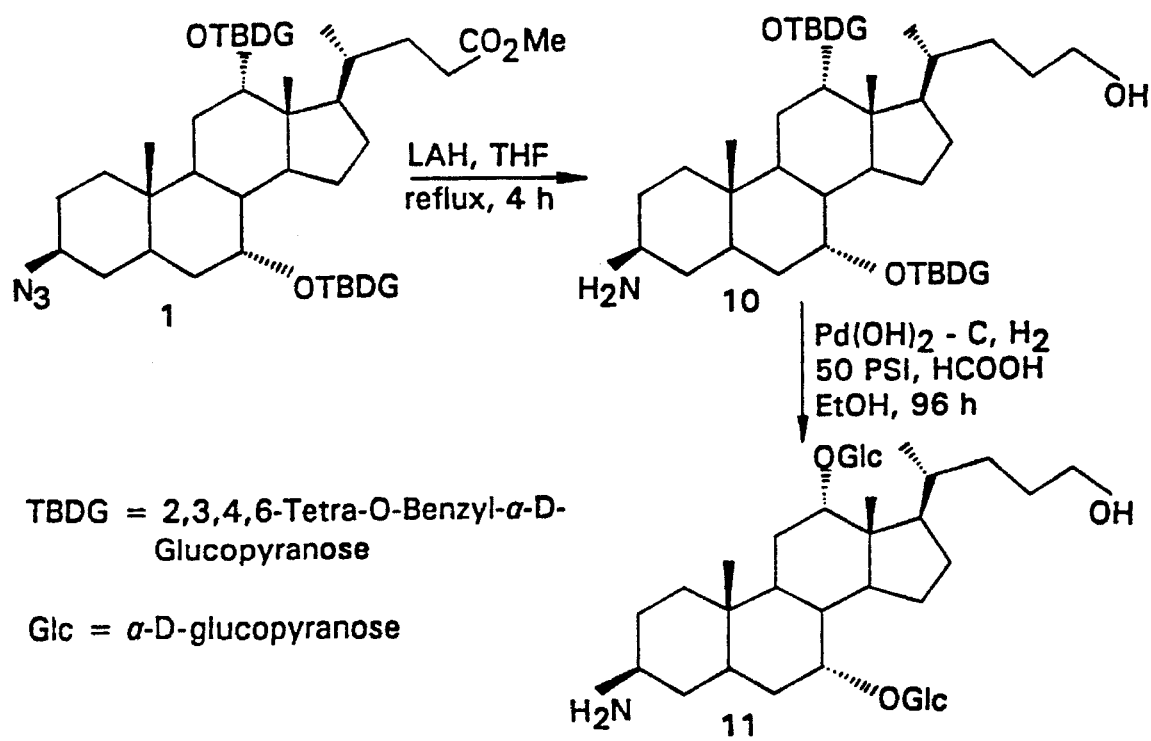
FIG. 2. Synthetic scheme for the preparation of 3β-amino-24-hydroxy-7α,12α-di(1'α-glucosyl)-5β-cholane.

Synthesis of 3β-Amino-24-hydroxy-7α,12α-di(1'α-glucosyl)-5β-cholane (11) (See, FIG. 2).

2.1. β-Amino-24-hydroxy-7α,12α-di(1'α-glucosyl)-5β-cholane (10).

To a mixture of lithium aluminum hydride (LAH, 0.19 g, 5 mmol) in anhydrous tetrahydrofuran (THF, 100 mL) is added dropwise at r.t. a solution of compound 1 (745 mg, 0.5 mmol) in THF (20 mL). The resulting reacting mixture is heated under reflux for 16 h, and then allowed to cool to r.t. Excess LAH is destroyed by the dropwise addition of aqueous sodium hydroxide (5 mL). The mixture is then acidified with 1N hydrochloric acid (7 mL) and extracted with methylene chloride (2×20 mL). The organic layer is washed with water (2×40 mL), dried ($Na_2SO_4$) and concentrated. The residue is purified by flash column chromatography (ethyl acetate:hexane =1:2) to provide 485 mg (70%) of 10 as a white foam (mp 54°–56° C.). TLC (solvent—$EtOH:CH_2Cl_2$=1:9) $R_f$=0.3. IR (KBr): 3087, 3063, 3030, 2921, 2865, 1454, 1160, 1070 $cm^{-1}$. $^1$H NMR ($CDCl_3$): δ7.38–6.85 (m, 40H), 5.06 (br d, 2H), 4.95–3.40 (m, 28H), 3.11 (br s, 1H), 2.62–0.72 (m, 39H). Fab MS: 1438 $(M+H)^+$. Anal. Calc. for $C_{92}H_{112}O_{13}N$: C, 76.73; H, 7.85; N, 0.97. Found: C, 76.28; H, 7.90; N, 0.97.

2.2. 3β-Amino-24-hydroxy-7α,12α-di(1'α-glucosyl)-5β-cholane (11).

Compound 10 (431 mg, 0.3 mmol) is hydrogenated by methods similar to those described above to give 129 mg (60%) of 11 as a white foam (mp 196°–198° C.). TLC (solvent—$MeOH: CH_2Cl_2$:Isopropylamine=2:2:1) $R_f$=0.15. IR (KBr): 3399, 2936, 2878, 2869, 1630, 1597, 1590, 1045, 1022 $cm^{-1}$. $^1$H NMR ($D_2O$): δ5.04 (d, 1H, J=3.6 Hz), 4.82 (d, 1H, J=3 Hz), 3.94 (br s, 1H), 3.74–3.22 (m, 12H), 2.47 (dd, 1H, J=12 Hz and 4 Hz), 2.20 (m, 2H), 1.95–0.90 (m, 36H). Fab Ms: 719 $(M+H)^+$. Anal. Calc. for $C_{36}H_{63}O_{13}N$. $4H_2O$: C, 54.72: H, 9.06: N, 1.77. Found: C, 54.52; H, 8.75, N, 1.67.

Example 3

Figure 3:
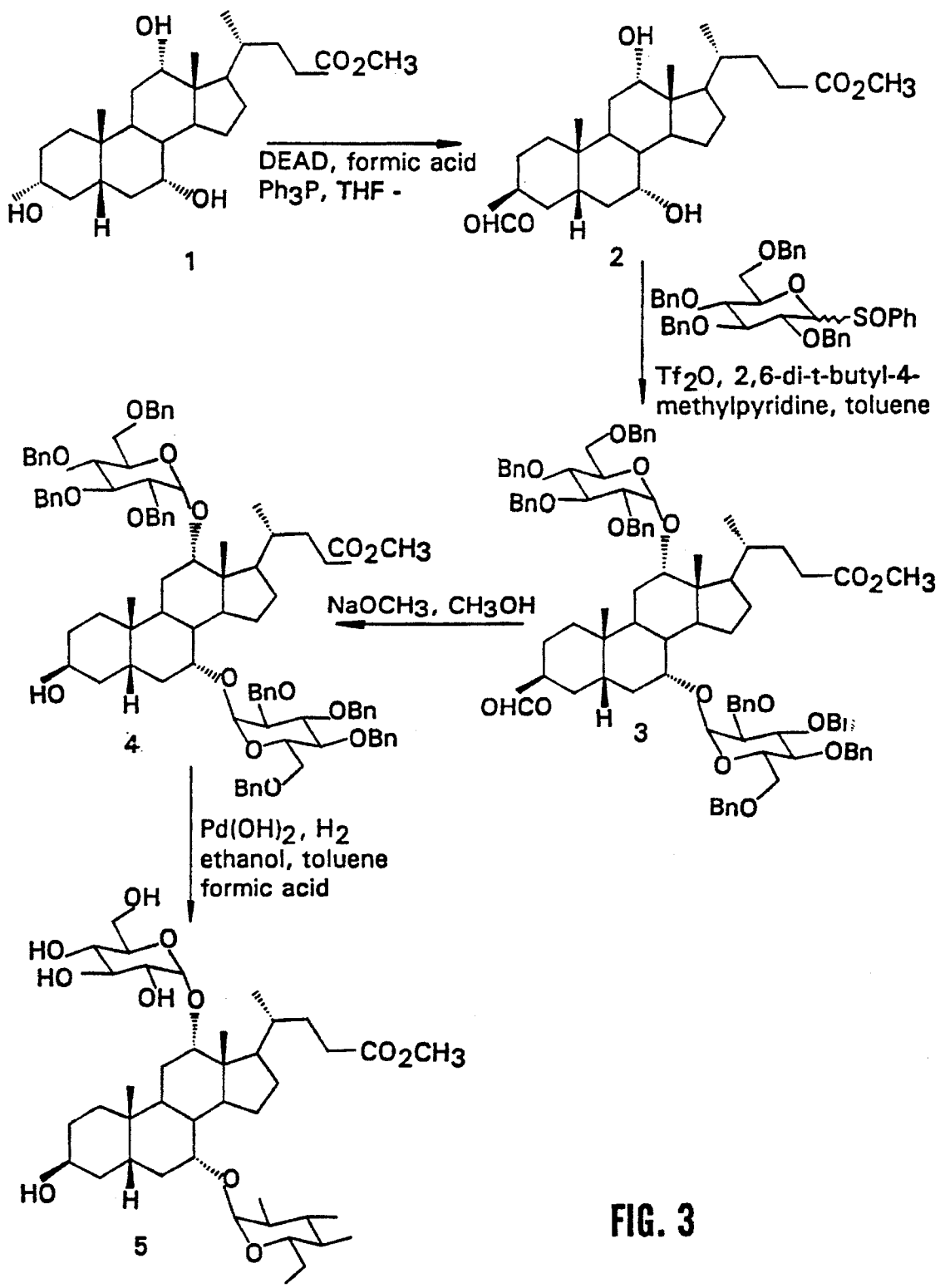
FIG. 3. Synthetic scheme for the preparation of methyl 3β-hydroxy-7α,12α-di(1'α-glucosyl)-5β-cholate.

Synthesis of Methyl 3β-hydroxy-7α,12α-di(1'α-glucosyl)-5β-cholate (5) (see, FIG. 3).

Kiesegel 60 F-254 TLC plate is used for all the TLC work unless otherwise indicated. FT-IR is performed on MIDAC Prospect IR instrument. NMR is performed on Varian VXR300s 300 MHz instrument. Chemical reagents are purchased from Aldrich or Fisher. Dry toluene is distilled from CaH$_2$. All other solvents are used directly from original container without further purification.

3.1. Methyl 3β-O-formylcholate (2).

To a solution of methyl cholate 1 (2.11 g, 5 mmol), formic acid (96%, 350 mg) and triphenyl phosphine (1.57 g, 6.0 mmol) in THF (75 mL) is added diethyl azodicarboxylate (DEAD, 1.05 g, 6.0 mmol) at room temperature (r.t.). The reaction mixture is stirred at r.t. for 16 h. Solvent is removed by evaporation. The residue is purified by use of a flash column (50%~60% ethyl acetate in hexane) to give 1.8 g (80%) of 2 as a thick oil: R$_f$ (60% ethyl acetate in hexane) 0.43; $^1$H NMR δ (CDCl$_3$) 0.76 (s, 3H), 0.99 (s, 3H), 1.12 (d, 3H), 1.2–2.6 (m, 24H), 3.66 (s, 3H), 3.87 (s, 1H), 3.99 (s, 1H), 5.15 (s, 1H), 8.04 (s, 1H).

3.2. Methyl 3β-O-formyl-7α,12α-O-di(1'α-(2',3',4', 6'-O-tetrabenzyl)glucosyl)-5β-cholate (3).

To a solution of phenyl 2,3,4,6, -O-tetrabenzylgluco-1-sulfoxide (6.33 g, 9.8 mmol) in 150 mL dry toluene is added triflic anhydride (1.66 mL, 9.8 mmol) at −78° C. After. 15 min. stirring at −78° C., 2,6-di-t-butyl-4-methylpyridine (2 g, 9.8 mmol) in a small amount of toluene is added, followed by 2 (2 g, 4.4 mmol) in a small amount of methylene chloride. The dry ice/acetone bath is then replaced with a dry ice/chloroform bath to keep the reaction temperature at about −60° C. with stirring for 2.5 h. Saturated aq. NaHCO$_3$ (100 mL) is then added. The reaction mixture is extracted with ethyl acetate (3×30 mL). The organic layer is dried and purified by flash column chromatography (20% ethyl acetate in hexane) to give 3 g (44%) of 3 as a thick oil: R$_f$ (20% ethyl acetate in hexane) 3.32; IR (neat) 3031, 2922, 1728, 1710, 1454 cm$^{-1}$; $^1$H NMR δ (CDCl$_3$) 0.72 (s, 3H), 0.96 (s, 3H),0.97 (d, 3H), 1.2–2.5 (m, 24H) 3.4–5.2 (m, 30H), 3.62 (s), 7.0–7.4 (m, 40H), 8.02 (s, 1H).

3.3. Methyl 3β-hydroxyl-7α,12α-O-di(1'α-2',3',4', 6'-O-tetrabenzyl)glucosyl)-5β-cholate (4).

To a solution of 3 (3 g, 2 mmol) in anhydrous methanol (100 mL) at 0° C. is added sodium methylate (138 mg, 2.6 mmol). The mixture is stirred at r.t for 2 h. Solvent is evaporated, and the residue is taken in methylene chloride, washed with a small amount of saturated aqueous ammonium chloride, and dried. Flash column chromatography (25% ethyl acetate in hexane) purification gives 750 mg (25%) of 4 as a thick oil: R$_f$ (30% ethyl acetate in hexane) 0.36; $^1$H NMR δ (CDCl$_3$) 0.73 (s, 3H), 0.97 (s, 3H), 1.02 (d, 3H), 1.2–2.5 (m, 24H), 3.61 (s), 3.4–4.9 (m, 30H, 5.04 (t, 1H), 6.9–7.4 (m, 40H). MS m/e 1489 (M$^+$+Na).

3.4 Methyl 3β-hydroxyl-7α,12α-O-di(1'α-glucosyl)-5β-cholate (5).

To a solution of 4 (750 mg) in toluene (5 mL) and ethanol (15 mL) is added Pd(OH)$_2$ (20% in carbon, 750 mg) and formic acid (95%, 0.7 mL). The mixture is hydrogenated at 50 psi for 18 h, the filtered. The filtrate is then evaporated. The residue is redissolved in methanol, filtered and evaporated again. The residue is then dissolved in a small amount of water, purified by reverse-phase column chromatography (60 mL MCI CHP-20P gel column; 25% H$_2$O in methanol). Lyophilization gives 260 mg (68%) of 5 as a white solid: R$_f$ (C-18 reverse phase, 30% H$_2$O in methanol) 0.28; mp. 170° C. (recrystallized with methanol-ethyl acetate, phase transfer); IR (KBr) 3430, 2880, 1722, 1439 cm$^{-1}$; $^1$H NMR (D$_2$O) δ0.62 (s, 3H), 0.75 (d, J=6.3Hz), 0.82 (s, 3H), 1.0–2.4 (m), 3.2–3.8 (m), 3.51 (s), 3.92 (s, 2H), 4.81 (d, J=3.6 Hz, 1H), 5.06 (d, J=3.9 Hz, 1H); MS m/e 769 (M$^+$+Na); Anal. Calc. (MW+2H$_2$O) C, 56.77; H, 7.99; Found C, 56.82; H, 8.22.

Example 4

Figure 4:
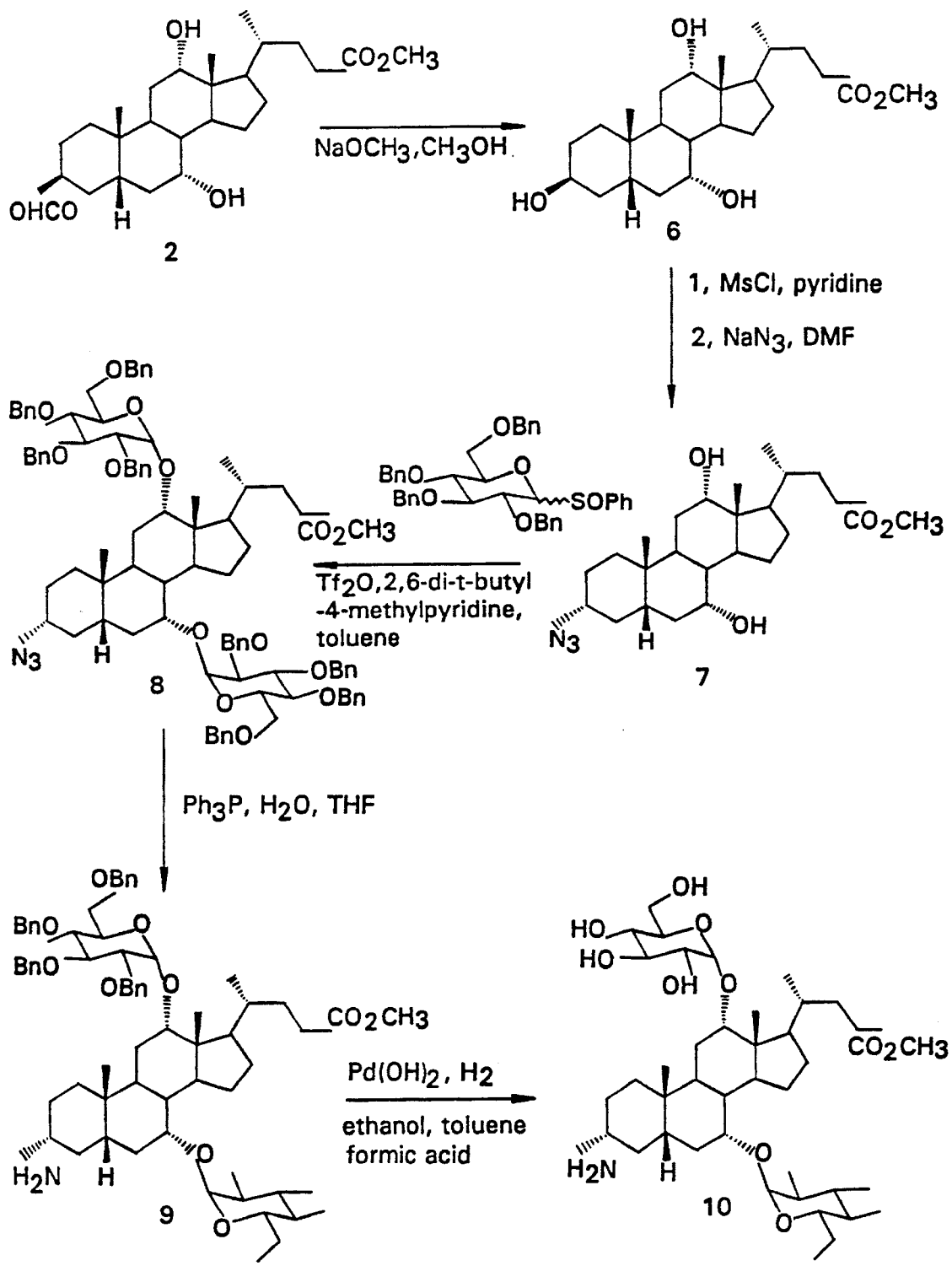
FIG. 4. Synthetic scheme for the preparation of methyl 3α-amino-7α,12α-di(1'α-glucosyl)-5β-cholate.

Synthesis of Methyl 3α-amino-7α,12α-di(1'α-glucosyl)-5β-cholate (10) (See, FIG. 4).

4.1. Methyl 3β-hydroxycholate (6).

Anhydrous methanol (10 mL) is added to a mixture of 2 (225 mg, 0.5 mmol) and sodium methylate (35 mg) at 0° C. The solution is stirred at r.t. for 0.3 h. Solvent is evaporated. The residue is taken up in methylene chloride, washed with conc. ammonium chloride, and dried. Removal of solvent gives 170 mg (84%) of 6 as a white solid: R$_f$ (90% ethyl acetate in hexane) 0.11; $^1$H NMR (CDCl$_3$) δ0.68 (s, 3H), 0.93 (s, 3H), 0.97 (d, J=6 Hz, 3H); 1.1–2.5 (m, 25H), 3.65 (s, 3H), 3.85 (s, 1H), 3.97 (m, 4.04 (s, 1H), 6.72 (br.s,).

4.2. Methyl 3α-azidocholate (7).

To a solution of 6 (2.73 g, 6.4 mmol) in dry pyridine at 0° C. is added methanesulfonyl chloride (0.6 mL, 7.7 mmol). The resulting mixture is stirred at 0° C. for 2 h and r.t. for 2 h. Solvent is evaporated; the residue is taken in methylene chloride, washed with conc. ammonium chloride, and dried. The crude mesylate is dissolved in DMF (40 mL) and treated with NaN$_3$ (2 g). The mixture is stirred while heated to 110° C. for 4 h. Solvent is removed. The residue is taken up in methylene chloride, washed with conc. ammonium chloride, and dried. Flash column chromatography (20% ethyl acetate in hexane) gives 1.15 g (40%) of 7 as a white solid: R$_f$ (30% ethyl acetate in hexane) 0.45; IR (KBr) 3477, 2939, 1732 cm$^{-1}$; $^1$H NMR (CDCl$_3$) δ0.68 (s, 3H), 0.90 (s, 3H), 0.96 (d, J=6.3 Hz, 3H), 1.1–2.5 (m, 24H), 3.14 (m, 1H), 3.66 (s, 3), 3.85 (d, J=2.7 Hz, 1H), 3.98 (s, 1H).

4.3. Methyl 3α-azido-7α,12α-O-di(1'α-(2',3',4',6'-O-tetrabenzyl)glucosyl)-5α-cholate (8).

To a solution of phenyl 2,3,4,6-O-tetrabenzyl gluco-1-sulfoxide (3.7 g, 5.7 mmol) in 120 mL dry toluene is added triflic anhydride (1.05 mL, 9.8 mmol) at −78° C. After 30 min. stirring at −78° C., 2,6-di-t-butyl-4-methylpyridine (1.17 g, 5.7 mmol) in a small amount of toluene is added, followed by 7 (1.15 g, 2.6 mmol) in 10 mL methylene chloride. The reaction mixture is stirred at −78° C. for 0.5 h. The dry ice/acetone bath is replaced with a dry ice/chloroform bath to keep the reaction temperature at about −60° C. for 2.5 h with stirring. 10% aq. NaHCO$_3$ is then added. The reaction mixture is extracted with ethyl acetate (3×50 mL). The organic layer is dried and purified by flash column chromatography (20% ethyl acetate in hexane) to give 1.10 g (28%) of 8 as a thick oil: R$_f$ (25% ethyl acetate in hexane) 0.50; IR (neat) 3030, 2927, 2091, 1736, 1455 cm$^{-1}$; $^1$H NMR (CDCl$_3$) δ0.72 (s, 3H), 0.94 (s, 3H), 1.0 (d, 3H), 1.1–2.5 (m, 24H), 3.64 (s), 3.1–5.1 (m, 30H), 6.9–7.4 (m, 40H). MS m/e 1515 (M$^+$+Na+H).

4.4. Methyl 3α-amino-7α,12αO-di(1'α-(2',3',4',6'-O-tetrabenzyl)glucosyl)-5α-cholate (9).

The compound 8 (1.1 g, 0.73 mmol) and triphenyl phosphine (0.62 g, 2.3 mmol) are dissolved in THF (30 mL) and H$_2$O (3 mL). The mixture is heated under reflux for 24 h. Solvent is evaporated. The residue is extracted with methylene chloride (3×20 mL) and dried. Flash column chromatography (2–3% methanol in chloroform) gives 640 ml (60%) of 9 as a thick oil: R$_f$ (10% methanol in chloroform) 0.45 (ninhydrin positive); $^1$H NMR (CDCl$_3$) δ0.71 (s, 3H), 0.92 (s, 3H), 0.98 d, 3H), 1.1–2.5 (m, 24H), 3.63 (s), 3.3–5.1 (m, 32H), 6.9–7.4 (m, 40H).

4.5. Methyl 3α-amino-7α,12α-O-di(1'α-glucosyl)-5β-cholate (10).

To a solution of 9 (640 mg) in 3 mL toluene and 30 mL ethanol is added Pd(OH)$_2$ (20% on carbon, 640 mg) and formic acid (96%, 0.64 mL). The mixture is hydrogenated at 50 psi for 24 h. Then, 0.64 mL additional 96% formic acid is added and the hydrogenation is continued for another 24 h. The mixture is filtered and evaporated. The residue is redissolved in H$_2$O and the pH of the aqueous solution is titrated to 9 with 10% $Na_2CO_3$. The solution is purified by reverse-phase column chromatography (60 mL MCI CHP-20p gel column; 25% $H_2O$ in methanol) to give 250 mg (77%) of 10 as white solid: $R_f$ (60% methanol, 20% methylene chloride, 20% isopropylamine) 0.25; mp. 190° C. (recrystallized with methanol-ethyl acetate, phase transfer); IR (KBr) 3396, 2938, 1736 $cm^{-1}$; $^1H$ NMR ($D_2O$) δ0.63 (s,3H), 0.78 (d, J=6 Hz, 3H), 0.85 (s, 3H), 1.0–2.4 (m, 24H), 2.92 (br. s, 1H), 3.2–3.8 (m), 3.54 (s), 3.94 (s, 2H), 4.84 (d, J=4.2 Hz, 1H), 5.05 (d, J=4.2 Hz, 1H); MS m/e 769 ($M^+$+Na+H); Anal. Calc. (MW+6$H_2O$) C, 52.05; H, 7.44; N, 1.64; Found C, 52.12; H, 7.82; N, 1.64.

Example 5

Figure 5:
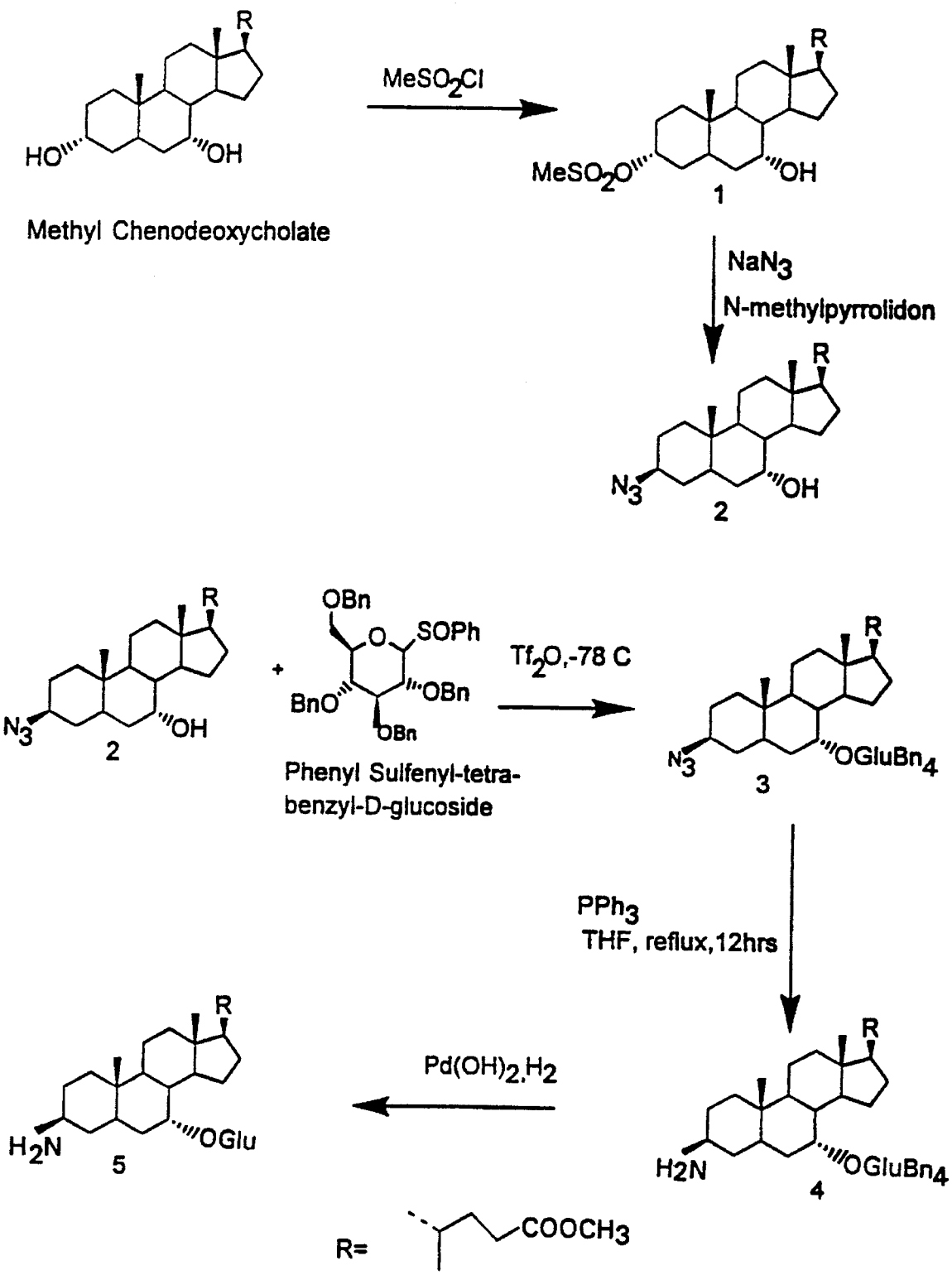
FIG. 5. Synthetic scheme for the preparation of methyl 3β-amino-7α-(1'α-glucosyl)chenodeoxycholate.

Synthesis of the methyl 3β-amino-7α-(1'α-glucosyl)chenodeoxycholate (5) (See, FIG. 5).

5.1. Methyl 3-O-methanesulfonyl-chenodeoxycholate (1).

Methyl chenodeoxycholate (27 g, 61.5 mmol) is dissolved in 100 mL dichloromethane (DCM), pyridine (20 mL). Dimethylaminopyridine (DMAP) (1.22 g, 10 mmol) is then added. The reaction mixture is chilled to 0° C., and methanesul-fonyl chloride (7.5 mL, 11.0 g, 96.7 mmol) is added dropwise. The reaction mixture is heated at 60° C. for 3 h, cooled to r.t., washed with 5% HCl, water, sodium bicarbonate, brine, and dried over sodium sulfate. The solvent is evaporated under reduced pressure (1 mm Hg, 80° C. in a bath) to give mesylate 1 as a thick oil, weight 27 g (90%). This material is used in the next step without further purification.

5.2. Methyl 3β-azido-chenodeoxycholate (2).

Methyl 3-O-methanesulfonyl-chenodeoxycholate (25 g, 51 mmol) and sodium azide (12 g, 185 mmol) are dissolved in 80 mL of N-methylpyrrolidone and heated at 110° C. (in an oil bath) for 3 h. The reaction mixture is cooled to r.t. and poured onto 300 g of ice to give an oil. The oil is extracted with toluene and purified by flash column chromatography (EA-Hexane from 0% to 40% of EA) to give substance 2, which crystallized from hexane. Weight 13 g (60%), m.p. 112°–113° C. (methanol). IR: 3380 (υOH), 2098 (υ$N_3$), 1738 $cm^{-1}$ (υCOOMe). $^1H$ NMR ($CDCL_3$) δ3.62 (s, 3H), 2.4–1.3 (26H), 0.983 (d, 3H), 0.955 (s, 3H), 0.685 (s, 3H).

5.3. Methyl 3β-azido-7α-O-(tetra-O-benzyl-α-D-glucosyl-1')chenodeoxycholate (3).

Phenyl sulfenyl-tetra-benzyl-D-glucoside (4.05 g, 6.25 mmol) in toluene (150 mL) is treated dropwise at −78° C. with triflic anhydride (1.06 mL, 6.25 mmol) in toluene (10 mL). 2,6-Diisopropyl-4-methyl-pyridine (1.3 g, 6.25 mmol) in toluene (10 mL) is added dropwise. Methyl 3-azido-deoxycholate 2 (2.16 g, 5 mmol) in toluene/dichloromethane (10 mL/10 mL) is added dropwise to the reaction mixture. The procedures are carried out at −78° C. under Ar. After the addition, the stirring is continued 1 h, followed by addition of a saturated solution of sodium bicarbonate (50 mL). The organic layer is washed with 5% HCl, water, brine, and dried over sodium sulfate. Evaporation of the solvent and purification by flash chromatography on silica gel with Ethylacetate (EA)/Hexane (gradient: from 0% to 25% of EA) affords 3.50 g (3.66 mmol, 73% yield) of 3. $R_f$=0.7 (silica, EA/Hexane 2/5), IR (neat) 2108, 1734 $cm^{-1}$; $^1H$ NMR ($CDCL_3$) δ7.2–7.44 (m, 20H), 4.31–4.45 (m, 15H), 3.62 (s, 3H), 0.850 (d, 3H), 0.671 (s, 3H), 0.649 (s, 3H).

5.4. Methyl 3β-amino-7α-O-(tetra-benzyl-α-D-glucosyl-1')chenodeoxycholate (4).

The azido derivate 3 (2.8 g, 3 mmol) and triphenylphosphine (1.85 g, 7.0 mmol) are dissolved in THF/water (99 mL/1 mL) and the reaction mixture is heated under reflux with stirring for 24 h. The solvent is removed at reduced pressure; the oil residue is dissolved in EA (50 mL), washed with sodium bicarbonate, then brine, then purified by flash chromatography in DCM/EtOH (gradient from 0% to 20% of EtOH) to give 1.5 g (50% yield) of 4, as a semi-solid: $R_f$=0.10 (silica, EA/Hexane 2/5), IR (neat) 3380, 1740 $cm^{-1}$; $^1H$ NMR ($CDCL_3$), δ7.15–7.8 (m, 20H), 4.40–5.1 (m, 15H), 3.65 (s, 3H), 0.888 (d, 3H), 0.670 (s, 3H), 0.630 (s, 3H).

5.5. Methyl 3β-amino-7α-O-(α-D-glucosyl-1')chenodeoxycholate (5).

The aminoderivative 4 (1.2 g, 1.3 mmol) is dissolved in 40 mL of EtOH, and a catalyst (10% $Pd(OH)_2$/C, 0.2 g) and formic acid (1 mL) are added. The reaction mixture is hydrogenated in a 0.5 L Parr® vessel at 50 psig for 48 h. The catalyst is filtered off, and the solvent is evaporated under reduced pressure to give a solid residue. Ethyl acetate (5 mL) is added to crystallize out the product. It is filtered and washed with hexane. Weight 0.27 g (yield 37%), m.p. 260° C. (decomposition). The substance is dissolved in water (5 mL) and freeze-dried. $R_f$=0.7 (silica, MeOH/DCM/isopropylamine 60/20/20); IR (KBr) υ$_{COOMe}$1734, υ$_{OH, NH}$3280–3440 $cm^{-1}$; $^1H$ NMR ($D_2O$) δ4.88 (s, 1H), 3.2–3.75 (m, 6H), 3.52 (s, 3H), 0.849 (s, 3H), 0.778 (d, 3H), 0.505 (s, 3H). Anal. Calcd. for $C_{31}H_{52}NO_8$ · HCOOH: C,62.5; H, 8.89; N, 2.28%. Found: C,59.0; H, 8.80; N, 2.25%. MS: M+$Na^+$. Calcd. 590. Found 590.

Example 6

Figure 6:
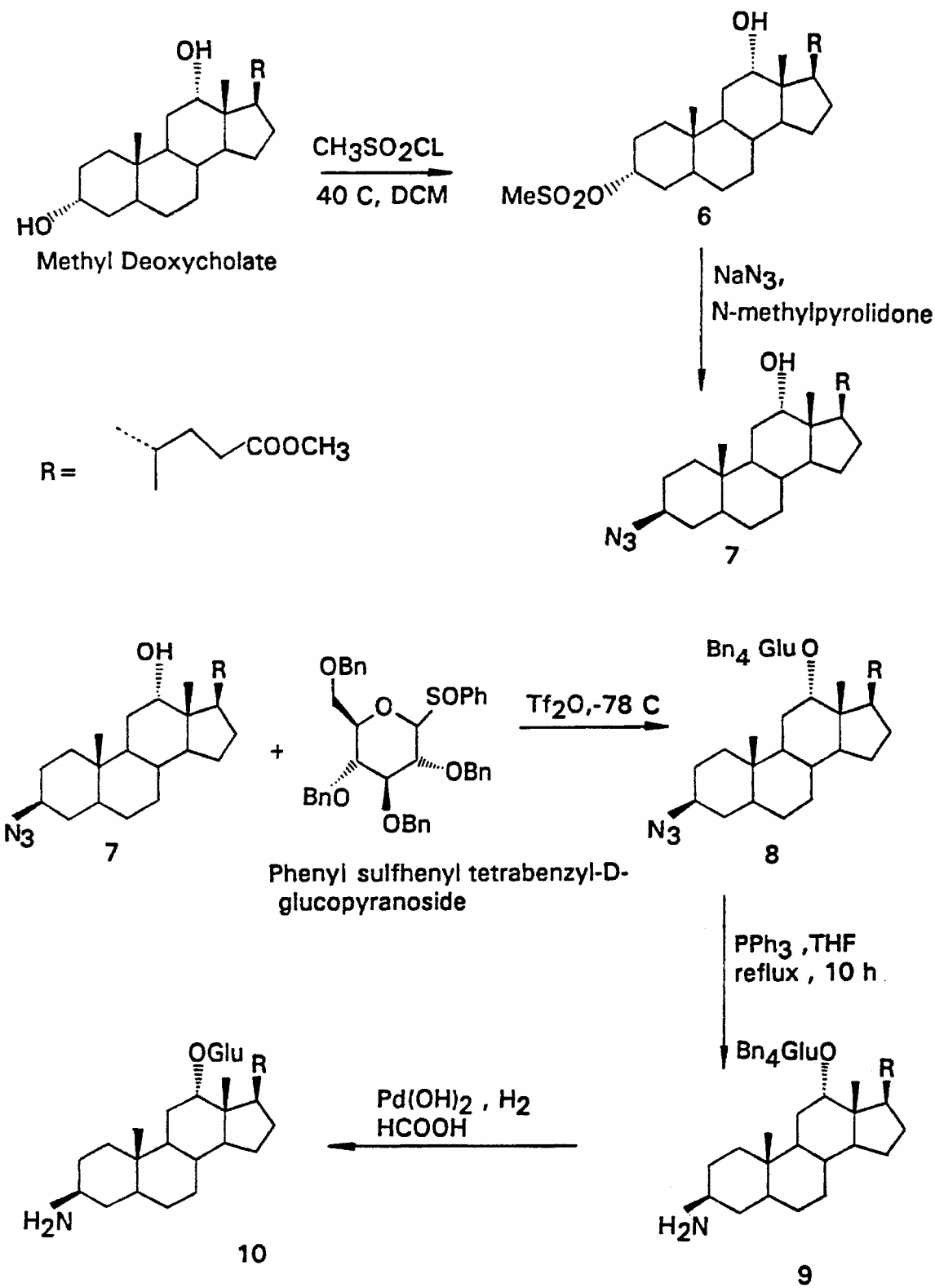
FIG. 6. Synthetic scheme for the preparation of methyl 3β-amino-12α-(1'α-glucosyl)deoxycholate.

Synthesis of 3-amino-12-O-glucosyl-deoxycholate (10) (See, FIG. 6).

6.1. 3α-O-Methanesulfonyl-deoxycholic acid, methyl ester (6).

The title compound is prepared in the same manner as the methyl 3-O-methanesulfonyl-chenodeoxycholate (1, FIG. 5). It is obtained as an oil and is used in the next step without further purification.

6.2. 3β-Azido-deoxycholic acid, methyl ester (7).

The title compound is prepared in the same manner as the methyl 3-azido-chenodeoxycholate (2, FIG. 5). Yield is 45%, m.p. 128° C. (from methanol). $R_f$=0.6 (silica, EA/Hexane 2/5). IR (KBr) υ$_{OH}$3380, υ$_{N3}$2089, υ$_{COOMe}$1734 $cm^{-1}$. $^1H$ NMR ($CDCL_3$) δ3.62 (s, 3H), 2.4–1.3 (m, 26H), 0.986 (d, 3H), 0.942 (s, 3H), 0.691 (s, 3H).

6.3. Methyl 3β-azido-12α-O-(tetra-O-benzyl-α-D-glucosyl-1')-deoxycholate (8).

The title compound is prepared in the same manner as substance 3 of FIG. 5. The yield is 40%. $R_f$=0.75 (silica, EA/Hexane 2/5). IR (neat) 2103, 1742 $cm^{-1}$. $^1H$ NMR ($CDCL_3$) δ7.23–7.32 (m, 20H), 4.44–4.97 (m, 15H), 3.67 (s, 3H), 0.854 (d, 3H), 0.688 (s, 3H), 0.643 (s, 3H).

6.4. Methyl 3β-amino-12α-O-(tetra-benzyl-α-D-glucosyl-1')-deoxycholate (9).

The title compound is prepared in the same manner as substance 4 of FIG. 6. The yield is 48%. $R_f$=0.12 (silica, EA/hexane); IR (neat) 1734, 3382 $cm^{-1}$. $^1H$ NMR ($CDCL_3$), δ7.1–7.9 (m, 20H), 4.40–4.95 (m, 15H), 3.642 (s, 3H), 0.867 (d, 3H), 0.676 (s, 3H), 0.628 (s, 3H).

6.5. Methyl 3β-amino-12α-O-(α-D-glucopyranosyl-1')-deoxycholate (10).

The title compound is prepared in the same manner as a substance 5 of FIG. 5. The yield is 71%, m.p. 250° C. (decomposition). $R_f$=0.7 (silica, DCM/MeOH/i-propylamine 60/20/20). IR (KBr) 3200–3428 υ$_{OH,NH}$, 1734 υ$_{COOMe}$ $cm^{-1}$; $^1H$ NMR ($D_2O$) δ4.95 (d, 1H), 3.85 (s, 1H), 3.69 (s, 1H), 3.62 (s, 1H), 3.38 (d, 2H), 3.53 (s, 3H), 0.85 (s, 3H), 0.78 (d, 3H), 0.51 (s, 3H). Anal. Calcd. for $C_{31}H_{52}NO_8 \cdot HCOOH$; C, 62.5; H, 8.89; N, 2.28%. Found: C, 61.5; H, 9.06; N, 2.22%. Mass-spectr: $M+Na^+$. Calcd. 590, found 590.

Example 7

Figure 7:
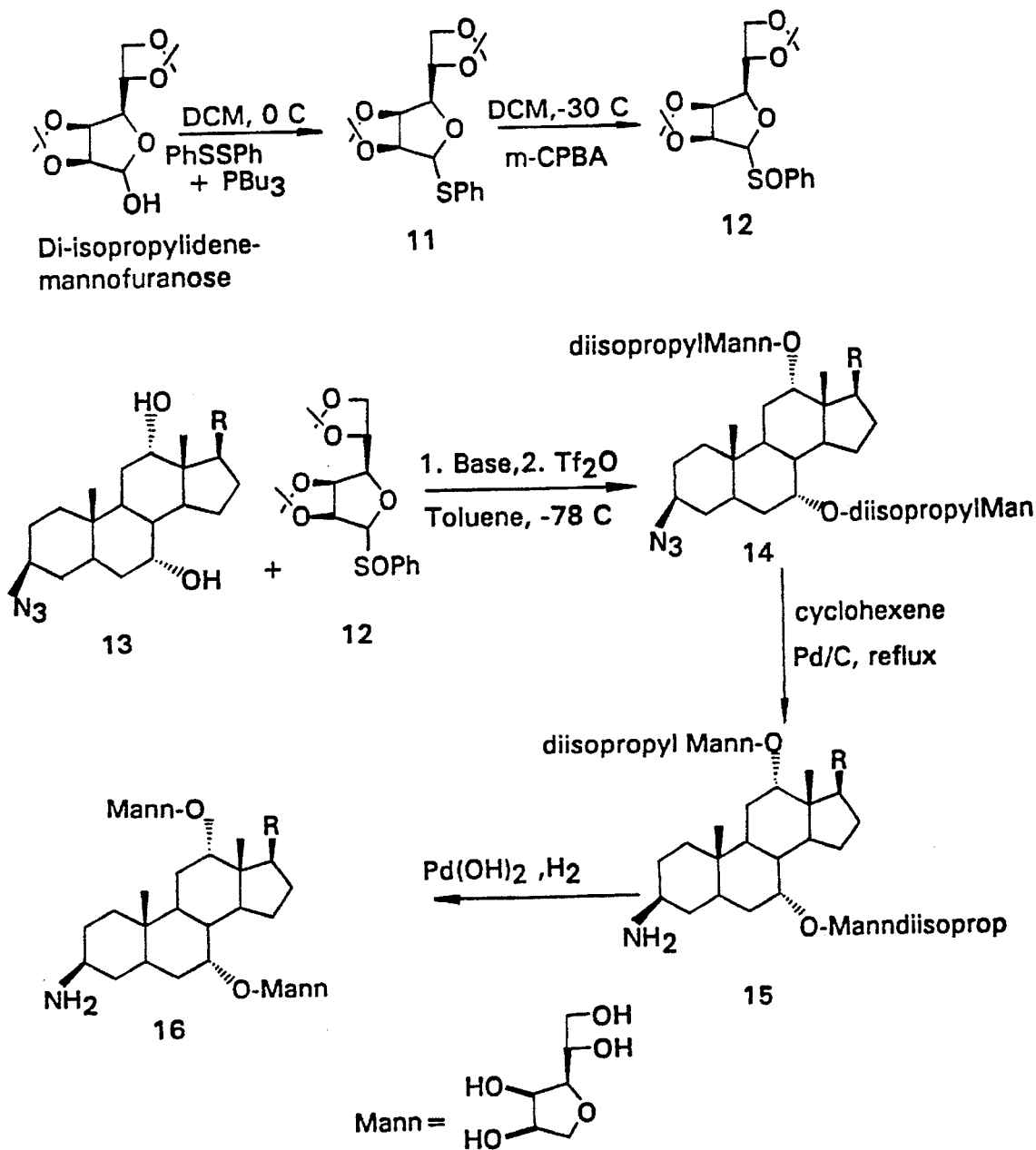
FIG. 7. Synthetic scheme for the preparation of methyl 3β-amino-7α,12α-bis(O-D-mannofuranosyl-1')cholate.

Synthesis of the methyl 3β-amino-7α,12α-bis(O-D-mannofuranosyl-1') cholate (16) (See, FIG. 7).

7.1. Phenyl 2:3,5:6-diisopropylidene-1-thiomannofuranoside (11).

A mixture of diisopropylidene-mannose (25 g, 96 mmol), phenyldisulfide (25 g, 115 mmol), and tributylphosphine (24.2 g, 20 mL, 120 mmol) in DCM (200 mL) is stirred at 0° C. for 4 h. The solvent and excess of tributylphosphine are then evaporated. Petroleum ether is added and a seed crystal, if available, is added to the stirred solution. The crystals are filtered after 10 h. Weight 22.6 g (yield 80%); m.p. 110° C. (from hexane). $R_f$=0.65 (silica, EA/Hexane 2/5).

IR (KBr) 3060, 3030, 1585, 1490, 1453, 1360, 1125, 1090, 1070 $cm^{-1}$. $^1H$ NMR ($CDCL_3$), δ7.7–7.0 (m, 5H), 3.95–5.1 (m, 7H), 1.25–150 (q, 12H).

7.2. Phenyl sulfenyl 2:3,5:6-diisopropylidenemannofuranoside (12).

Mannosylsulfide 11 (22 g, 62 mmol) is dissolved in DCM (150 mL) and chilled to −78° C. Then, m-CPBA (17 g, 70 mmol) in EA (100 mL) is added dropwise over 1 h. When TLC shows the spot of the product 12 only, a saturated solution of sodium bisulfite (100 mL) is poured into the reaction mixture. The organic layer is washed with sodium bicarbonate, brine, dried and evaporated to give an oil, which is purified by flash chromatography (EA/Hexane, gradient from 0% to 50% of EA). Two fractions are collected. The first one $R_f$=0.15 (EA/Hexane 2/5), weight 5.0 g, does not work in the coupling reaction and may be discarded. The second one ($R_f$=0.10, weight 15 g, 65% yield) works in the coupling reaction. Melting point 110° C. IR (KBr) 3060, 3030, 2900, 2870, 1490, 1370, 1230, 1130, 1090 $cm^{-1}$. $^1H$ NMR ($CDCL_3$) δ7.7–7.1 (m, 5H), 5.1–4.4 (m, 7H), 1.5–1.25 (m, 12H).

7.3. Methyl 3β-azido-7α,12α-bis(O-2:3,5:6-diisopropylidene-D-mannofuranosyl-1') cholate (14).

The sulfoxide 12 (0.96 g, 2.5 mmol), the methyl 3β-azidocholate 13 (2.5 mmol), and 2,6-diisopropyl-4-methyl-pyridine (0.63 g, 3.3 mmol) are dissolved in 100 mL of toluene and chilled to −78° C. under Ar. Triflic anhydride (0.56 mL, 3.3 mmol is then added). After the addition, stirring is continued for 1 h at −78° C. The reaction mixture is then allowed to warm to −25° C. during 1 h. The reaction is quenched with a saturated solution of the sodium bicarbonate (50 mL) and the organic layer is washed with water, brine, dried over sodium sulfate and evaporated under reduced pressure. The residue is dissolved in hexane (25 mL), the insoluble part being filtered off. The clear filtrate is purified by flash chromatography (silica, EA/Hexane, gradient from 0% to 25% of EA). The pure substance 14 is isolated as a thick oil: weight 0.45 g (60% yield). $R_f$=0.65 (silica, EA/Hexane 2/5). IR (neat) 2108, 1734 $cm^{-1}$. $^1H$ NMR ($CDCL_3$) δ 5.18–3.95 (m,14H), 3.68 (s, 3H), 1.4 –1.2 (m, 24H), 0.96 (d, 3H), 0.88 (s, 3H), 0.59 (s, 3H).

7.4. Methyl 3β-amino-7α,12α-bis(O-D-mannofuranosyl-1')cholate (16).

The purified azidoderivative 14 (0.4 g, 04 mmol) is dissolved in methanol/hexene (10 mL/15 mL) and 10% Pd/C (100 mg) is added. The reaction mixture is refluxed under Ar with stirring for 24 h. TLC (silica, EA/Hexane 2/5) shows the disappearance of the starting material and the appearance of a new spot on the base line. The catalyst is filtered off, and the filtrate is evaporated under reduced pressure to give the amino derivate 15 as a thick oil. $R_f$=0.8 (silica, DCM/EtOH 10/1), IR (neat) 3400 ($v_{NH}$), 1742 ($v_{COOMe}$). The isopropylidene protecting groups of 15 are hydrolyzed and isolated without further purification as shown in FIG. 18. The crude oil is dissolved in 80% acetic acid (10 mL) and heated under reflux for 6 h. The reaction mixture is diluted with water (20 mL), and a slight precipitate is filtered off. The clear filtrate is evaporated under reduced pressure to give a semi-solid residue of 16. This solid is rinsed with ethyl acetate (5 mL), filtered, dried in a dessicator, dissolved in water, and purified by reverse phase column chromatography (CHP-20P column; 0–50% methanol-water). Any chromatography solvent is removed under reduced pressure. Freeze-drying affords the substance 16 as a white powder (0.155 g, 50% yield). $R_f$=0.8 (silica DCM/MeOH/iso-Propylamine 6/2/2); IR (neat) $v_{OH,NH}$3400, $v_{COOMe}$1734 $cm^{-1}$; $^1H$ NMR ($CD_3OD$) δ5.13 (d, 2H), 4.1–3.2 (m, 14H), 3.53 (s, 3H), 1.0–1.2 (m, 25H), 0.817 (d, 3H), 0.744 (s, 3H), 0.465 (s, 3H). Anal. Calcd. for $C_{37}H_{63}NO_{14}$: C, 59.6; H, 8.44; N, 1.87%. Found: C, 58.8; H, 8.33; N, 2.37%. MS: $M-OH+Na^+$=750. Found 750.

Example 8

Figure 8:
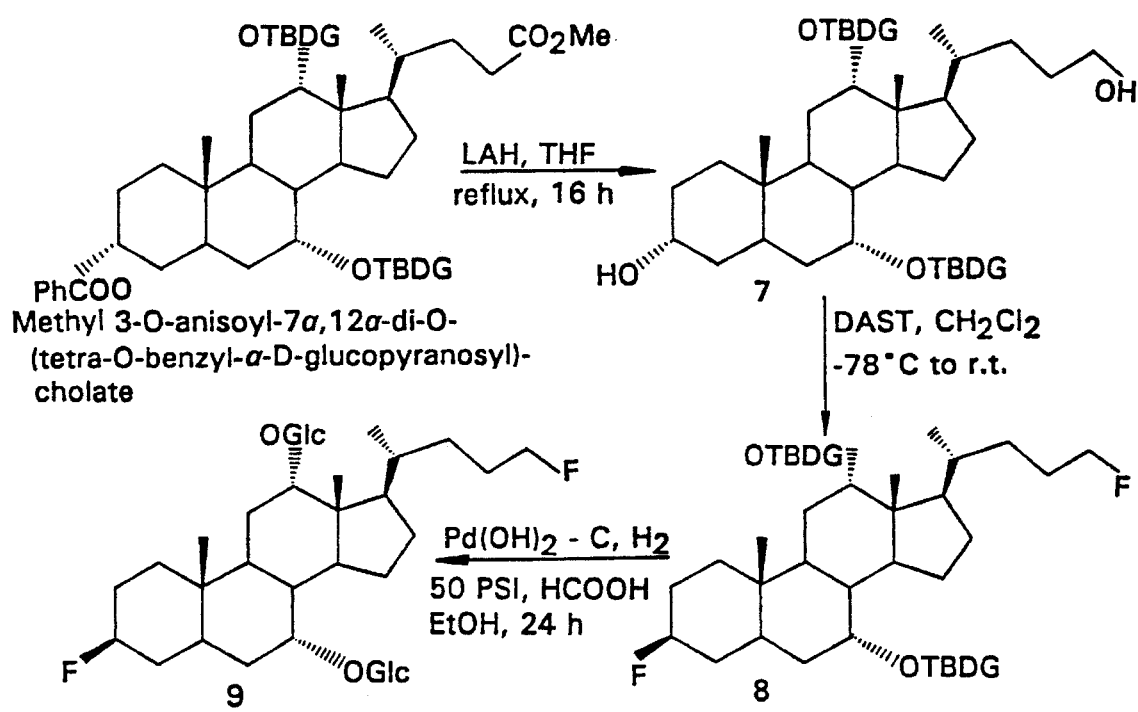
FIG. 8. Synthetic scheme for the preparation of 3β,24-Difluoro-7α,12α-di(1'α-glucosyl)-5β-cholane.

Synthesis of 3β,24-Difluoro-7α,12α-di(1'α-glucosyl)-5β-cholane (9) (See, FIG. 8).

8.1. 3α,24-Di-hydroxy-7α,12α-di-(2',3',4', 6'-tetra-O-benzyl-1'α-glucosyl)-5β-cholane (7).

To a mixture of lithium aluminum hydride (1.14 g, 30 mmol) in anhydrous tetrahydrofuran (100 mL), methyl 3-O-anisoyl-7α,12α-di(2',3',4',6'-tetra-O-benzyl-1'α-glucosyl)-5β-cholate (4.8 g, 3 mmol) in anhydrous tetrahydrofuran (100 mL) is added slowly at room temperature. Afterward, the contents of the reaction vessel are heated under reflux for 16 h. The mixture is then allowed to cool and excess lithium aluminum hydride is destroyed by the dropwise addition of aqueous sodium hydroxide (30 mL). The reaction mixture is acidified with 1N hydrochloric acid (40 mL) and extracted with methylene chloride (2×100 mL). The organic layer is washed with water (2×200 mL), dried ($Na_2SO_4$), and concentrated. The residue on flash chromatography (EtOAC:Hexane=1:2) gives 7 (2.6 g, 60%) as a white foam (mp 48°–50° C.). TLC $R_f$ (solvent—EtOAC:Hexane=1.2) 0.5. IR (KBr): 3445, 3086, 3057, 2930, 2868, 1491, 1457, 1364, 1153, 1073 $cm^{-1}$. $^1H$ NMR ($CDCl_3$): δ7.50–6.90 (m, 40H), 5.05–3.40 (m, 30H), 2.50–0.70 (m, 41H). Fab MS: 1462 $(M+Na)^+$. Anal. Calc. for $C_{92}H_{110}O_{14}$: C, 76.73; H, 7.71. Found: C, 76.04; H, 7.65.

8.2 3β,24-Difluoro-7α,12α-di-(2',3',4', 6'-tetra-O-benzyl-1'α-glucosyl)-5β-cholane (8).

To a cooled (−78° C.) solution of compound 7 (1.45 g, 1 mmol) in anhydrous methylene chloride (50 mL), is added diethylaminosulfur trifluoride (0.35 mL, 2.65 mmol) with stirring for 15 min. The temperature is raised slowly to r.t. (over 30 min) and then saturated aqueous sodium bicarbonate (50 mL) is added. The reaction mixture is stirred for 15 min. The organic layer is separated, washed with water (2×50 mL), dried ($Na_2SO_4$), and concentrated. The residue, on flash chromatography (EtOAC:Hexane=3.17), gives 8 (700 mg, 49%) as an oil. TLC $R_f$ (solvent—EtOAC:Hexane=1:3) 0.7. IR (KBr): 3090, 3065, 3032, 2923, 2878, 1492, 1456, 1362, 1208, 1075 $cm^{-1}$. $^1H$ NMR ($CDCl_3$): δ7.40–6.90 (m, 40H), 5.08 9d, 1H, J=3 Hz), 5.05 (d, 1H, J=3 Hz), 4.95–3.40 (m, 28H), 2.70–0.70 (m, 39H). Fab MS:

1465 (M+Na)$^+$. Anal. Calc. for $C_{92}H_{108}O_{14}F_2$: C, 76.53; H, 7.54. Found: C, 76.40; H, 7.68.

8.3.    3β,24-Difluoro-7α,12α-di-(1'α-glucosyl)-5β-cholane (9).

Compound 8 (577 mg, 0.4 mmol) is subjected to hydrogenolysis to give (173 mg, 60%) as a white foam (mp 180°–182° C.). TLC R$_f$ (solvent—MeOH: CH$_2$Cl$_2$Isopropylamine=2:2:1) 0.7. IR (KBr): 3087, 3063, 3030, 2921, 2865, 1454, 1160, 1070 cm$^{-1}$. $^1$H NMR (DMSO-d$_6$ and two drops of D$_2$O): δ4.85 (d, 1H, J =4.2 Hz), 4.67 (d, 1H, J=#.6 Hz), 4.43 (t, 1H, J=5.6 Hz), 4.27 (t, 1H, J=5.6 Hz), 3.89 (s, 1H), 3.60–3.00 (m, 7H), 2.47–0.6 (m, 37H). Fab MS: 746 (M+Na)$^+$. Anal. Calc. for $C_{36}H_{60}O_{12}F_2 \cdot 2H_2O$: C, 56.96; H, 8.50. Found: C, 57.04; H, 8.47.

Other embodiments of the present invention will be evident to one of ordinary skill in view of the detailed descriptions provided herein. Such embodiments are considered to fall within the scope and spirit of the present invention, which invention is not limited to the preferred embodiments described above but only by the following claims.

What is claimed is:

1. A process for the production of 3-amino-substituted glycosylated bile acid derivatives comprising:

(a) providing an ester of a bile acid having a hydroxyl substituent at the 3-position of the steroid nucleus;

(b) converting said hydroxyl subtituent at the 3-position into a leaving group;

(c) displacing said leaving group with an azido group with inversion of the stereochemistry at the 3-position to provide a 3-azido-substituted bile acid ester intermediate;

(d) subjecting said 3-azido-substituted bile acid ester intermediate to reaction conditions which effect the glycosylation of any free hydroxyl group present in said steroid nucleus; and (e) reducing said azido substituent to provide a 3-amino-substituted glycosylated bile acid ester derivative.

2. The process of claim 1 which further comprises removing any protecting groups, if present, from the glycosyl moieties of said ester derivative.

3. The process of claim 2 which further comprises hydrolyzing said ester derivative to provide the free acid derivative.

4. The process of claim 1 which further comprises purifying said ester derivative by reverse-phase column chromatography.

5. The process of claim 1 which further comprises recrystallizing an intermediate or reaction product after a reaction step.

6. The process of claim 1 which further comprises recrystallizing a reagent before its use in a reaction step.

7. The process of claim 1 in which said leaving group is a tosylate, mesylate or triflate.

8. The process of claim 1 in which said reduction step is effected by ammonium formate and palladium on carbon.

9. The process of claim 1 in which said reduction step is effected by triphenyl phosphine.

10. The process of claim 1 in which said reduction step is effected by Raney nickel.

11. The process of claim 1 in which said glycosylation conditions include a sulfoxide-based glycosylation procedure.

12. The process of claim 1 in which said bile acid is cholic acid, allocholic acid, deoxycholic acid or chenodeoxycholic acid.

13. The process of claim 1 in which said ester includes a methyl ester.

14. The process of claim 1, in which the conversion takes place in the presence of an organic solvent.

15. The process of claim 14, in which the organic solvent is dry pyridine, methylene chloride or methylene chloride/pyridine mixtures, optionally in the presence of dimethylaminopyridine.

16. The process of claim 1, in which step (b) is performed at about 0° C.

17. The process of claim 1, in which the leaving group is displaced with sodium azide.

18. The process of claim 17, in which said sodium azide is present in excess.

19. The process of claim 1, in which the leaving group is displaced with an azido group in the presence of a solvent.

20. The process of claim 19, in which the solvent is selected from the group consisting of dimethyl formamide and N-methylpyrrolidone.

21. The process of claim 1, in which the displacement reaction is carried out at an elevated temperature.

22. The process of claim 1, in which the reaction conditions comprise dissolving the 3-azido-substituted bile acid ester intermediate in toluene, mixing with a desired glycosyl sulfoxide, and treating with an activating agent at low temperature to initiate a condensation reaction.

23. The process of claim 1, in which reduction is effected by treatment with triphenyl phosphine.

24. The process of claim 1, in which reduction is effected by treatment with lithium aluminum hydride.

25. The process of claim 1, in which reduction is carried out at an elevated temperature.

26. The compound 3β-azido-7α, 12α-di(1'α-glucosyl)-5β-cholic acid, its salt, ester or amide.

27. The compound 3α-azido-7α,12α-di(1'α-glucosyl)-5β-cholic acid, its salt, ester or amide.

* * * * *